United States Patent [19]

Costa et al.

[11] Patent Number: 5,206,382
[45] Date of Patent: Apr. 27, 1993

[54] INDOLE DERIVATIVES, PHARMACEUTICAL COMPOSITIONS AND METHODS OF TREATING NEUROLOGICAL AND PSYCHIATRIC DISORDERS

[75] Inventors: Erminio Costa, Chevy Chase, Md.; Alessandro Guidotti, Washington, D.C.; Alan Kozikowski, Ponte Vedra Beach; Dawei Ma, Jacksonvile, both of Fla.

[73] Assignee: Fidia Georgetown Institute for the Neurosciences, Washington, D.C.

[21] Appl. No.: 722,196

[22] Filed: Jun. 27, 1991

[51] Int. Cl.$^5$ ............... C07D 401/12; C07D 403/12; C07D 407/14; C07D 409/04; A61K 209/20
[52] U.S. Cl. ..................... 548/494; 548/466; 548/465; 546/208; 514/330; 514/414; 514/415
[58] Field of Search ............ 548/494, 465, 466; 546/208; 514/330, 414, 415

[56] References Cited

FOREIGN PATENT DOCUMENTS 5151505 11/1980 Japan.

OTHER PUBLICATIONS

Julie et al. Ann. Inst. Pasteur 109 (3), 343-362 (1965). Chemical Abstract 64:677b (1965).

*Primary Examiner*—David B. Springer
*Attorney, Agent, or Firm*—Birch, Stewart, Kolasch & Birch

[57] ABSTRACT

A compound having the formula:

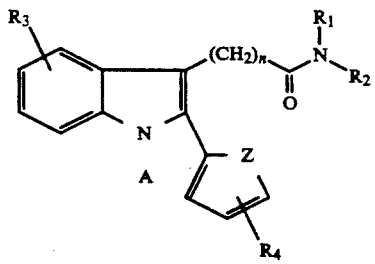

wherein $R_1$ and $R_2$ independently is selected from the group consisting of H, $C_3$–$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring; $R_3$ is H, $C_1$–$C_{12}$ straight or branched alkyl, $NO_2$, $NH_2$, $N_3$, CN, halogen, $CO_2R$, OR, or SR wherein R is H or lower alkyl; $R_4$ is H, $C_1$–$C_{12}$ straight or branched alkyl, $NO_2$, $NH_2$, $N_3$, CN, halogen, $CO_2R$, OR, or SR wherein R is H or lower alkyl; A is nothing or a $C_1$–$C_5$ alkylene to form a ring; Z is O, NH, S or —CH=CH—; and n is an integer of 1–3; or a pharmaceutically acceptable salt thereof. The compounds are useful in compositions and methods for treating psychiatric and neurological disorders.

23 Claims, No Drawings

INDOLE DERIVATIVES, PHARMACEUTICAL COMPOSITIONS AND METHODS OF TREATING NEUROLOGICAL AND PSYCHIATRIC DISORDERS

BACKGROUND OF THE INVENTION

In the mammalian central nervous system (CNS), including man, there are two types of benzodiazepine (BZD) recognition sites, each thought to be associated with a specific protein. The "central" BZD recognition site is associated with the α- subunit of $GABA_A$ receptors and participates in the gating of chloride (Cl) channels operated by GABA. The "mitochondrial" BZD recognition site (MBR) is associated with a protein in the outer mitochondrial membrane that participates in the regulation of cholesterol access to the mitochondrial inner membrane, where a specific type of cytochrome $P_{450}$ catalyzes the side cleavage of cholesterol to form pregnenolone. Both BZD recognition sites are widely represented in the brain. The central type BZD recognition sites are present in neurons whereas the MBRs are abundant in astroglial cells.

Stimulation of MBR by appropriate ligands (e.g. 4-Cl-Diazepam and Alpidem) facilitates cholesterol influx into mitochondria and the formation of pregnenolone, the parent molecule of endogenous steroids. The BZD-induced activation of mitochondrial steroidogenesis occurs in glial cells, which are rich in MBR and produce steroids that can regulate the $GABA_A$-operated Cl channel. These steroids act on recognition sites located in the transmembrane region of $GABA_A$ receptors and affect the channel gating process. Some pregnenolone derivatives, e.g. 3-α-hydroxy-5α-pregnan-20-one(3-αOH-DHP) and 3α,21-dihydroxy-5α-pregnan-20-one(THDOC) positively modulate, and others (pregnenolone sulphate) negatively modulate GABA action. Because these steroids appear to occur naturally in the brain, they are termed neurosteroids.

Research on BZD ligands by the present inventors, targeted to BZD recognition sites located on mitochondria of glial cells, has been carried out in order to provide drugs that can be used to modify neurosteroid production and to rectify neuropsychiatric abnormalities (pathological anxiety, panic, depression etc.) that have as an etiopathogenesis, an alteration in GABAergic function.

It is known that 4-Cl-Diazepam (a high affinity ligand for the MBR that also binds to the $GABA_A$ receptor) in small doses causes a proconflict response (i.e., anxiety) in rats that is partially resistant to Flumazenil, a specific antagonist of BZD at the $GABA_A$ receptors but which is sensitive to PK-11195, a partial agonist at the MBR. On the other hand, Alpidem (an imidazopyridine that has high affinity for the MBR and BZD recognition sites on $GABA_A$ receptors) causes a dose-related anticonflict (anxiolytic) action that is reduced by both PK-11195 and Flumazenil.

Thus, it is difficult to ascribe a behavioral effect on the MBR or modulation of GABA receptors by Alpidem and 4-Cl-Diazepam.

The compounds of the present invention modulate the MBR receptor, and their anxiolytic action can be related exclusively to the binding of MBR since they fail to bind to the BZD receptor site located on GABA receptors or to binding sites for other known putative neurotransmitters.

SUMMARY OF THE INVENTION

The present invention is directed to compounds having the formula

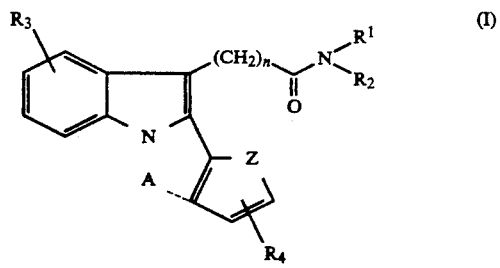

(I)

wherein $R_1$ and $R_2$ independently can be selected from the group consisting of H, $C_3$–$C_{12}$ straight or branched alkyl, aryl, or lower alkyl-substituted aryl; or $R^1$ and $R^2$ may join to form a 4-to 6-membered saturated or unsaturated ring or a 4-to 6-membered saturated or unsaturated lower alkyl-substituted ring;

$R^3$ can be H, $C_1$–$C_{12}$ straight or branched alkyl, $NO_2$, $NH_2$, $N_3$, CN, halogen, $CO_2R$, OR, or SR wherein R is H or lower alkyl;

$R^4$ can be H, $C_1$–$C_{12}$ straight or branched alkyl, $NO_2$, $NH_2$, $N_3$, CN, halogen, $CO_2R$, OR, or SR wherein R is H or lower alkyl;

A can be a $C_1$–$C_5$ alkylene group to form a ring; Z can be O, NH, S or —CH=CH—; and n is an integer of 1–3; or a pharmaceutically acceptable salt thereof.

The present invention is also directed to a pharmaceutical composition which comprises an antianxiety effective amount of a compound having the formula

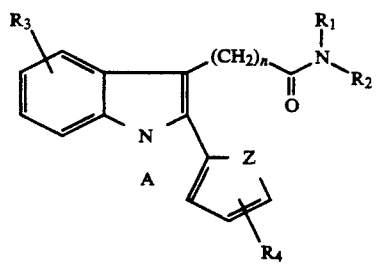

wherein $R^1$ and $R^2$ independently can be the same or different and are selected from the group consisting of H, $C_3$–$C_{12}$ straight or branched alkyl, aryl or lower alkyl-substituted aryl; or $R_1$ and $R^2$ may join to form a 4-to 6-membered saturated or unsaturated ring or a 4-to 6-membered saturated or unsaturated lower alkyl-substituted ring;

$R^3$ can be H, $C_1$–$C_{12}$ straight or branched alkyl, $NO_2$, $NH_2$, $N_3$, CN, halogen, $CO_2R$, OR, or SR wherein R is H or lower alkyl;

$R^4$ can be H, $C_1$–$C_{12}$ straight or branched alkyl, $NO_2$, $NH_2$, $N_3$, CN, halogen, $CO_2R$, OR, or SR wherein R is H or lower alkyl;

A can be a $C_1$–$C_5$ alkylene group to form a ring; Z can be O, NH, S or —CH=CH—; and n is an integer of 1–3; or a pharmaceutically acceptable salt thereof; and a pharmaceutically acceptable carrier.

The present invention is also directed to a method for treating neurological and psychiatric disorders which comprises administering to a patient in need thereof, a therapeutically effective amount of a compound having the above formula (I) wherein $R_1$ and $R_2$ independently is selected from the group consisting of H, $C_1$-$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is H, $C_1$-$C_{12}$ straight or branched alkyl, $NO_2$, $NH_2$, $N_3$, CN, halogen, $CO_2R$, OR, or SR wherein R is H or lower alkyl;

R is H, $C_1$-$C_{12}$ straight or branched alkyl, $NO_2$, $NH_2$, $N_3$, CN, halogen, $CO_2R$, OR, or SR wherein R is H or lower alkyl;

A is nothing or a $C_1$-$C_5$ alkylene to form a ring; Z is O, NH, S or —CH=CH—; and n is an integer of 1-3; or a pharmaceutically acceptable salt thereof or compositions thereof.

DESCRIPTION OF THE PREFERRED EMBODIMENTS

The present invention includes pharmaceutically acceptable salts of the above-described compounds of formula (I) are included within the scope of this invention. Examples of such salts include, but are not limited to, oxalate, citrate, tartrate, hydrochloride and like salts.

In one particular embodiment, the compound of the present invention has the formula

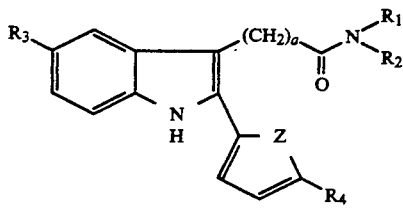

wherein $R_1$ and $R_2$ independently is selected from the group consisting of H, $C_3$-$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is H, $C_1$-$C_{12}$ straight or branched alkyl, $NO_2$, $NH_2$, $N_3$, CN, halogen, $CO_2R$, OR, or SR wherein R is H or lower alkyl;

$R_4$ is H, $C_1$-$C_{12}$ straight or branched alkyl, $NO_2$, $NH_2$, $N_3$, CN, halogen, $CO_2R$, OR, or SR wherein R is H or lower alkyl;

Z is O, $NH_2$, S, or —CH=CH—; and n is an integer of 1-3; or a pharmaceutically acceptable salt thereof.

In another particular embodiment, the compound of the present invention has the formula

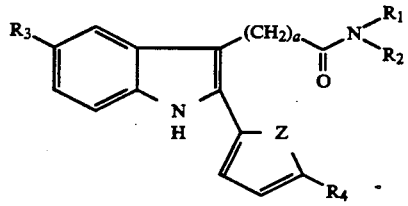

wherein $R_1$ and $R_2$ independently is selected from group consisting of H, $C_3$-$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is $C_1$-$C_{12}$ straight or branched alkyl, $NO_2$, $NH_2$, $N_3$, CN, halogen, $CO_2R$, OR, or SR wherein R is H or lower alkyl;

$R_4$ is $C_1$-$C_{12}$ straight or branched alkyl, $NO_2$, $NH_2$, $N_3$, CN, halogen, $CO_2R$, OR, or SR wherein R is H or lower alkyl;

Z is O, NH, S, or —CH=CH—; and n is an integer of 1-3; or a pharmaceutically acceptable salt thereof.

In still another particular embodiment, the compound of the present invention has the formula

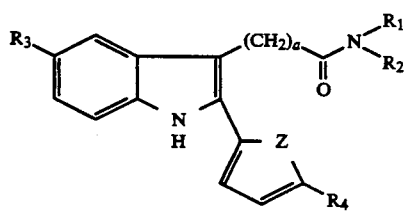

wherein $R_1$ and $R_2$ independently is selected from the group consisting of H, $C_4$-$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is H, $C_1$-$C_{12}$ straight or branched alkyl, $NO_2$, $NH_2$, $N_3$, CN, halogen, $CO_2R$, OR, or SR wherein R is H or lower alkyl;

$R_4$ is H, $C_1$-$C_{12}$ straight or branched alkyl, $NO_2$, $NH_2$, $N_3$, CN, halogen, $CO_2R$, OR, or SR wherein R is H or lower alkyl;

Z is O, NH, S, or —CH=CH—; and n is an integer of 1-3; or a pharmaceutically acceptable salt thereof.

$R_1$ and $R_2$ can be $C_3$-$C_{12}$ alkyl and advantageously $C_4$-$C_{10}$ alkyl. By alkyl is meant straight or branched aliphatic radicals having from 3 to 12 carbon atoms such as n-pentyl, n-hexyl and n-heptyl, n-octyl, n-nonyl and n-decyl. A preferred alkyl radical is n-hexyl.

By aryl is meant an organic radical derived from an aromatic hydrocarbon which can further be substituted. An example of such an aryl radical is phenyl.

By lower alkyl-substituted aryl is meant a lower alkyl group having 1 to 4 carbon atoms which is directly attached to the aromatic hydrocarbon. Examples of lower alkyl-substituted aryl include, but are not limited to, 1-methyl-phenyl, 1-ethylphenyl, 1-propylphenyl, and the like.

In the compounds of formula (I), $R^1$ and $R^2$ can each independently be H, $C_3$-$C_{12}$ straight or branched alkyl, aryl, or lower alkyl-substituted aryl; however, $R^1$ and $R^2$ cannot both be hydrogen.

$R^1$ and $R^2$ can also be joined to form a 4-to 6-membered saturated or unsaturated ring. Examples of such rings include, but are not limited to

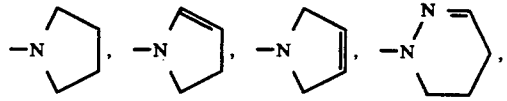

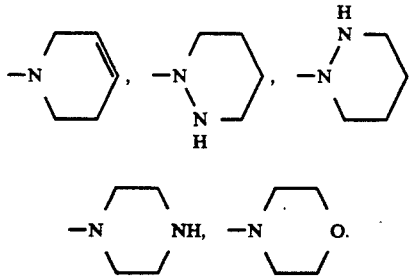

The 4-to 6-membered ring may additionally contain an additional nitrogen, oxygen or sulfur atom.

R can be lower alkyl. By lower alkyl is meant a $C_1$–$C_4$ straight or branched chain aliphatic radical. Examples of lower alkyl include, but are not limited to, methyl, ethyl, n-propyl, i-propyl and n-butyl and the like.

The term "halogen" includes the non-metallic elements of the seventh group of the Periodic Table, i.e., F, Cl, Br and I. Particularly preferred halogen atoms are F and Cl.

Method and Preparation of the Compounds of the Present Invention

The following examples further illustrate the present invention. It is to be understood, however, that the invention is not limited solely to the particular examples described herein. All percentages used herein are by weight, unless otherwise specified.

Materials: 3-benzoylpropionic acid 1c, 1d, and 1h were prepared by the addition reaction of the corresponding aryl aldehyde to acrylonitrile or methacrylonitrile followed by hydrolysis; 1e, 1f, and 1g were obtained by the standard Friedel-Crafts reaction of the requisite aryl compounds and succinic anhydride.

General Reaction Scheme. The ketoacid 1 below is converted to its mixed anhydride and reacted with the amine of choice to provide the corresponding ketoamide. The ketoamide is heated in turn with the aromatic hydrazine of choice to provide the corresponding hydrazone. The hydrazone product is then heated with zinc chloride to bring about the Fisher indolization reaction. Purification of the resulting solid generally by recrystallization affords the desired indole product (e.g., compound 2, infra).

Preparation of the starting ketoacid 1 can be accomplished by the addition of the appropriate aryl aldehyde to acrylonitrile or methacrylonitrile followed by hydrolysis. Alternatively, a standard Friedel-Crafts acylation reaction between the requisite aryl compound and succinic anhydride or a larger ring anhydride can be used.

For the preparation of those indole derivatives containing a ring labeled as "A" in the Formula (I), the appropriate 3-substituted indole derivative is first treated with a base and then with a haloalkyl-substituted aryl halide to furnish an N-substituted indole. The N-substituted indole is then subjected to a cyclization reaction employing a palladium catalyst to bring about ring closure to the indole 2-position. "A" can vary in size and can be comprised of from one to five carbon atoms.

EXAMPLE 1

Procedure for conversion of 3-benzoylpropionic acid 1 to indole amide 2: 3-benzoylpropionic acid (1) (25 mmol) and triethylamine (87.5 mmol) were dissolved in 150 ml of tetrahydrofuran (THF) and cooled to −40° C. To this stirred solution, ethyl chloroformate (27.5 mmol) was added dropwise, and then the reaction suspension was stirred for 30 minutes at −20° C. before the addition of 27.5 mmol of dipropylamine. The suspension solution was allowed to warm to ambient temperature, and stirring was continued for another 1 hour. The reaction was quenched by introducing 100 ml of $H_2O$, and the resulting mixture was extracted with ether (400 ml). The ethereal extracts were washed successively with aqueous 5% HCl (100 ml) and saturated brine (100 ml×2), and dried over $Na_2SO_4$. The crude amide 2 was obtained by removing the solvent under reduced pressure, then mixing the residue with the corresponding hydrazine (25 mmol) and heating at 100° C. for 30 minutes. The water was removed by vacuum, and the hydrazone was treated with 5 parts of powdered anhydrous zinc chloride. The mixture was heated at 170° C. for 5 minutes stirring vigorously by hand. The cooled mixture was dissolved in 100 ml of acetone and diluted with 500 ml of ether and 100 ml of $H_2O$. The organic layer was washed with 5% aqueous HCl solution (100 ml) and saturated brine (100 ml×2) in succession, and dried over $Na_2SO_4$. After evaporation to dryness, the pale yellow solid was recrystallized from ethyl acetate and n-hexane (1:10–1:1) to give Compound No. 2 in pure form as a white crystalline solid.

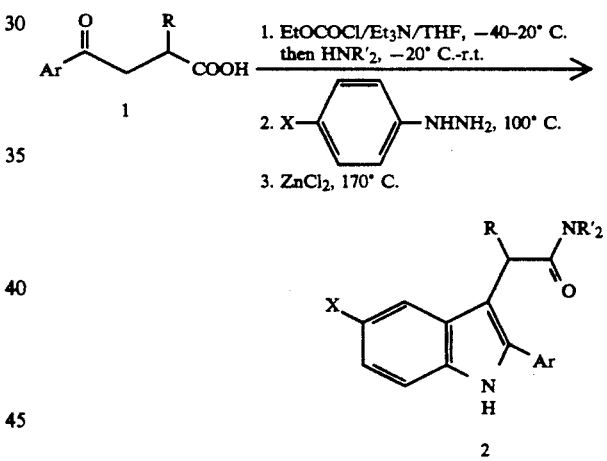

a. R = H, Ar = Ph
b. R = H, Ar = p-ClC$_6$H$_4$
c. R = H, Ar = m-ClC$_6$H$_4$
d. R = H, Ar = p-FC$_6$H$_4$
e. R = H, Ar = p-BrC$_6$H$_4$
f. R = H, Ar = p-MeC$_6$H$_4$
g. R = H, Ar = C$_4$H$_3$S
h. R = Me, Ar = p-ClC$_6$H$_4$
a. X = R = H, R' = n-Pr, Ar = C$_6$H$_5$, 83%
b. X = R = H, R' = n-Pr, Ar = p-ClC$_6$H$_4$, 86%
c. X = R = H, R' = n-Pr, Ar = m-ClC$_6$H$_4$, 79%
d. X = R = H, R' = n-Pr, Ar = p-FC$_6$H$_4$, 73%
e. X = R = H, R' = n-Pr, Ar = p-BrC$_6$H$_4$, 81%
f. X = R = H, R' = n-Pr, Ar = C$_4$H$_3$S, 50%
g. X = Cl, R = H, R' = n-Pr, Ar = C$_4$H$_3$S, 51%
h. X = Cl, R = H, R' = n-Pr, Ar = p-ClC$_6$H$_4$, 85%
i. X = Me, R = H, R' = n-Pr, Ar = p-MeC$_6$H$_4$, 52%
j. X = Me, R = H, R' = Me, Ar = p-MeC$_6$H$_4$, 71%
k. X = R = H, R' = Me, Ar = C$_6$H$_5$, 58%
l. X = H, R = Me, R' = n-Pr, Ar = p-ClC$_6$H$_4$, 41%
m. X = H, R = H, R' = n-C$_6$H$_{13}$, Ar = p-FC$_6$H$_4$
n. X = Cl, R = H, R' = n-C$_6$H$_{13}$, Ar = p-ClC$_6$H$_4$

The yield, melting point and spectral data for compounds 2a–2n are as follows:

2a: 83%, mp 123.5°–124.5° C.; IR (KBr) 3269, 3058, 1623, 1429 cm$^{-1}$; $^1$H NMR (CDCl$_3$, 300 MHz) δ 8.18 (s, 1H), 7.76 (d, 1H), 7.56 (d, 2H), 7.43 (dd, 2H), 7.37 (d, 1H), 7.33 (d, 1H), 7.08–7.20 (m, 2H), 3.91 (s, 2H), 3.25 (t, 2H), 3.06 (t, 2H), 1.23–1.55 (m, 4H), 0.79 (t, 3H), 0.62 (t, 3H); $^{13}$C NMR (CDCl$_3$, 300 MHz) 170.8, 136.1, 135.5, 132.8, 129.1, 128.9, 128.4, 127.9, 122.4, 119.9, 119.8, 110.8, 107.1, 49.8, 47.9, 32.4, 31.2, 22.2, 20.9, 11.4, 11.0; mass spectrum (15 ev) m/Z 334 (M+), 206, 203, 55; exact mass calcd for C$_{22}$H$_{26}$N$_2$O 334.2045; found 334.2045.

2b: 86, mp 177.5°–178.5° C.; IR (KBr) 3273, 2964, 1627, 1486, 1455 cm$^{-1}$; $^1$H NMR (CDCl$_3$, 300 MHz) 8.32 (s, 1H), 7.61 (d, 1H), 7.46 (d, 2H), 7.37 (d, 2H), 7.20–7.23 (m, 1H), 6.06–7.16 (m, 2H), 3.85 (s, 2H), 3.29 (t, 2H), 3.15 (t, 2H), 1.35–1.58 (m, 4H), 0.83 (t, 3H), 0.73 (t, 3H); $^{13}$C NMR (CDCl$_3$, 300 MHz) 169.8, 136.0, 134.0, 132.2, 131.5, 129.6, 128.8, 128.6, 121.7, 119.0, 118.8, 111.1, 106.9, 48.9, 46.9, 30.0, 21.8, 21.5, 11.2, 10.8; mass spectrum (15 ev) m/Z 368 (M+), 370 (M++2), 240, 205, 177, 149, 128, 99, 86, 69, 55; exact mass calcd for C$_{22}$H$_{25}$ClN$_2$O 368.1655; found 368.1655.

2c: 79%, mp 160°–161° C.; IR (KBr) 3586, 1624, 1558, 1456 cm$^{-1}$; $^1$H NMR (CDCl$_3$, 300 MHz) δ 8.19 (s, 1H), 7.66 (d, 1H), 7.60 (s, 1H), 7.38 (d, 1H), 7.30–7.35 (m, 3H), 7.18 (dd, 1H), 7.11 (dd, 2H), 3.88 (s, 2H), 3.29 (t, 2H), 3.15 (t, 2H), 1.50 (m, 4H), 0.84 (t, 3H), 0.73 (t, 3H); $^{13}$C NMR (CDCl$_3$, 300 MHz) δ 170.7, 136.3, 134.7, 134.6, 134.1, 130.1, 129.0, 127.9, 127.7, 126.3, 122.8, 120.0, 119.4, 111.1, 107.9, 49.9, 48.1, 30.6, 22.3, 21.0, 11.5, 11.2; mass spectrum (15 ev) m/Z 368 (M+), 370 (M++2), 240, 205, 128, 86; exact mass calcd for C$_{22}$H$_{25}$ClN$_2$O 368.1655; found 368.1655.

2d: 73%; mp 140°–141° C.; IR (KBr) 3570, 1621, 1554, 1453 cm$^{-1}$; $^1$H NMR (CDCl$_3$, 300 MHz) δ 8.11 (s, 1H), 7.66 (d, 1H), 7.55 (m, 2H), 7.33 (d, 1H), 6.90–7.21 (m, 4H), 3.85 (s, 2H), 3.27 (t, 2H), 3.15 (t, 2H), 1.46 (m, 4H), 0.82 (t, 3H), 0.70 (t, 3H); $^{13}$C NMR (CDCl$_3$, 300 MHz) δ 170.8, 162.6 (d, J=246.2 Hz), 136.0, 134.7, 130.1 (d, J=6.8 Hz), 129.1, 129.0, 122.5, 120.1, 119.5, 115.9 (d, J=21.8 Hz), 110.9, 107.2, 49.9, 48.0, 30.8, 22.3, 21.0, 11.4, 11.0; mass spectrum (15 ev) m/Z 352 (M+), 224, 128, 43; exact mass calcd for CH$_{22}$H$_{25}$FN$_2$O 352.1951; found 352.1951.

2e: 81%; mp 188°–189° C.; IR (KBr) 3586, 1624, 1560, 1456 cm$^{-1}$; $^1$H NMR (CDCl$_3$, 300 MHz) δ 8.15 (s, 1H), 7.64 (d, 1H), 7.58 (d, 2H) 7.43 (d, 2H), 7.32 (d, 1H), 7.18 (dd, 1H), 7.11 (d, 1H), 3.85 (s, 2H), 3.28 (t, 2H), 3.15 (t, 2H), 1.45 (m, 4H), 0.84 (t, 3H), 0.73 (t, 3H); $^{13}$C NMR (CDCl$_3$, 300 MHz) δ 170.8, 136.7, 134.5, 132.0, 131.7, 129.9, 129.1, 122.7, 121.9, 119.9, 119.2, 111.1, 107.6, 50.0, 48.0, 30.8, 22.3, 22.0, 11.5, 11.2; mass Spectrum (15 ev), m/Z 412 (M+), 414 (M++2), 284, 205, 128, 102, 86, 77; exact mass calcd for CH$_{22}$H$_{25}$BrN$_2$O 412.1150; found 412.1150.

2f: 50%, mp 153°–154° C.; IR (KBr) 3582, 1625, 1561, 1452 cm$^{-1}$; $^1$H NMR (CDCl$_3$, 300 MHz) δ 8.11 (s, 1H), 7.70 (d, 1H), 7.38 (d, 1H), 7.32 (d, 1H), 7.25 (m, 1H), 7.08–7.19 (m, 3H), 3.98 (s, 2H), 3.26 (t, 2H), 3.12 (t, 2H), 1.37–1.54 (m, 4H), 0.82 (t, 3H), 0.70 (t, 3H); $^{13}$C NMR (CDCl$_3$, 300 MHz) 170.5, 136.1, 134.2, 129.2, 129.0, 127.8, 125.6, 125.5, 122.7, 119.9, 119.6, 110.8, 107.6, 49.8, 47.9, 31.5, 22.2, 20.9, 11.4, 11.1; mass spectrum (15 ev) m/Z 340 (M+), 212, 194, 167, 55; exact mass calcd for C$_{20}$H$_{24}$N$_2$OS 340,1609; found 340.1609.

2g: 51%, mp 161°–162° C.; IR (KBr) 3586, 1624, 1558, 1454 cm$^{-1}$; $^1$H NMR (CDCl$_3$, 300 MHz) δ 8.47 (s, 1H), 7.55 (m, 1H), 7.39 (d, 1H), 7.15 (d, 1H), 7.02–7.12 (m, 3H), 3.91 (s, 2H), 3.33 (t, 2H), 3.21 (t, 2H), 1.48–1.63 (m, 4H), 0.87 (t, 3H), 0.80 (t, 3H); $^{13}$C NMR (CDCl$_3$, 300 MHz) 170.6, 134.7, 134.0, 131.4, 127.6, 125.2, 125.1, 122.3, 117.7, 112.2, 106.3, 50.0, 48.2, 30.4, 22.3, 21.1, 11.5, 11.3; mass spectrum (15 ev) m/Z 374 (M+), 376 (M++2), 319, 274, 246, 210, 128, 86, 69, 59, 43; exact mass calcd for C$_{20}$H$_{25}$ClN$_2$OS 374.1220; found 374.1220.

2h: 85%, mp 178°–180° C.; IR (KBr) 3283, 1625, 1482, 1435 cm$^{-1}$; $^1$H NMR (CDCl$_3$, 300 MHz) δ 8.83 (s, 1H), 7.41 (s, 1H), 7.27–7.30 (m, 4H), 6.91–6.97 (m, 2H), 3.75 (s, 2H), 3.38 (t, 2H), 3.25 (t, 2H), 1.46–1.65 (m, 4H), 0.93 (t, 3H), 0.85 (t, 3H); $^{13}$C NMR (CDCl$_3$, 300 MHz) δ 171.2, 136.2, 134.9, 133.5, 130.9, 130.0, 128.8, 128.7, 125.5, 122.4, 117.4, 112.4, 106.6, 50.1, 48.2, 29.8, 22.4, 21.1, 11.5, 11.4; mass spectrum (15 ev) m/Z 402 (M+), 404 (M++2), 374, 370, 239, 204, 91; exact mass calcd for C$_{22}$H$_{24}$Cl$_2$N$_2$O 402.1266; found 402.1266.

2i: 85%, mp 184°–185° C.; $^1$H NMR (CD$_3$COCD$_3$, 300 MHz) 10.11 (s, 1H), 7.49 (d, 2H), 7.40 (s, 1H), 7.28 (d, 2H), 7.25 (d, 1H), 6.84 (d, 1H), 3.85 (s, 2H), 3.21 (t, 2H), 3.12 (t, 2H), 2.85 (s, 3H), 2.80 (s, 3H), 1.31–1.48 (m, 4H), 0.75 (t, 3H), 0.63 (t, 3H); $^{13}$C NMR (CDCl$_3$, 300 MHz) 171.0, 137.5, 135.6, 134.3, 130.0, 129.4, 129.3, 128.9, 128.1, 123.7, 119.2, 110.4, 106.0, 49.7, 47.8, 31.4, 22.0, 21.6, 21.2, 20.8, 11.4, 10.9; mass spectrum (15 ev) m/Z 362 (M+), 261, 234, 219, 204; exact mass calcd for C$_{24}$H$_{30}$N$_2$O 362.2358; found 362.2358.

2j: 52%, mp 181°–182° C.; IR (KBr) 3579, 1623, 1584, 1483 cm$^{-1}$; $^1$H NMR (CDCl$_3$, 300 MHz) δ 7.99 (s, 1H), 7.41–7.46 (m, 3H), 7.24–7.29 (m, 3H), 7.02 (d, 1H), 3.89 (s, 2H), 2.92 (s, 3H), 2.83 (s, 3H), 2.46 (s, 3H), 2.42 (s, 3H); $^{13}$C NMR (CDCl$_3$, 300 MHz) 171.5, 137.7, 135.8, 134.3, 130.1, 129.6, 129.4, 129.2, 128.2, 123.9, 119.1, 110.5, 105.7, 37.5, 35.8, 31.3, 21.6, 21.3; mass spectrum m/Z 306 (M+) 234, 228, 204, 176, 115, 91, 72.

2k: 78%, mp 173.5°–174.5° C.; IR (KBr) 3482, 3057, 1637, 1494, 1448 cm$^{-1}$; $^1$H NMR (CDCl$_3$, 300 MHz) 8.29 (s, 1H), 7.68 (d, 1H), 7.54 (d, 2H), 7.45 (m, 2H), 7.32–7.37 (m, 2H), 7.09–7.18 (m, 2H), 3.91 (s, 2H), 2.90 (s, 3H), 2.82 (s, 3H); $^{13}$C NMR (CDCl$_3$, 300 MHz) 171.3, 136.4, 135.7, 135.1, 129.3, 128.8, 128.5, 127.9, 122.4, 120.0, 119.6, 110.9, 106.9, 37.4, 35.8, 31.2; mass spectrum m/Z 306 (M+), 234, 204, 176, 115, 91, 72.

2l: 41%, mp 260°–261° C.; IR (KBr) 3580, 1624, 1599, 1558, 1461 cm$^{-1}$; $^1$H NMR (CDCl$_3$, 300 MHz) δ 8.03 (s, 1H), 7.98 (d, 1H), 7.45–7.52 (m, 4H), 7.35 (d, 1H), 7.18 (dd, 1H), 7.10 (dd, 1H), 4.08 (q, 1H), 2.49–3.35 (m, 4H), 1.72 (d, 3H), 1.31–1.47 (m, 2H), 1.00–1.14 (m, 2H), 0.70 (t, 3H), 0.32 (t, 3H); $^{13}$C NMR (CDCl$_3$, 300 MHz) δ 172.5, 136.2, 134.3, 132.9, 131.4, 129.4, 129.3 127.7 122.8 121.5 120.2 114.3, 110.7, 49.0, 48.0, 34.7, 22.0, 20.4, 19.4, 11.4, 10.6; mass spectrum (15 ev) m/Z 382 (M+), 384 (M++2), 256, 254, 204, 126, 43; exact mass calcd for C$_{23}$H$_{27}$ClN$_2$O 382.1812; found 382.1812.

2m: mp 97°–98° C.; IR (KBr) 3198, 2953, 1620, 1501, 1458, 1224 cm$^{-1}$; $^1$H NMR (CDCl$_3$, 300 MHz) δ 8.14 (s, 1H), 7.65 (d, J=7.7 Hz, 1H), 7.54 (m, 2H), 7.32 (d, J=7.6 Hz, 1H), 7.08–7.20 (m, 4H), 3.84 (s, 2H), 3.29 (t, 2H), 3.17 (t, 2H), 1.37–1.45 (m, 4H), 1.09–1.22 (m, 10H), 1.03 (m, 2H), 0.85 (t, 6H); $^{13}$C NMR (CDCl$_3$, 300 MHz) 170.6, 162.6 (d, J=246.6 Hz), 136.0, 134.6, 130.1 (d, J=7.9 Hz), 129.1, 129.0, 122.6, 120.1, 119.6, 116.1 (d, J=21.6 Hz), 110.8, 107.3, 48.3, 46.3, 31.7, 31.6, 30.9, 29.1, 27.8, 26.8, 26.5, 22.7, 22.6, 14.1, 14.0; mass spectrum m/z 436 () 407, 294, 251, 224, 196, 147, 128, 85.

2n: mp 78°–79° C.; IR (KBr) 3189, 2963, 1624, 1503, 1468 cm$^{-1}$; $^1$H NMR (CDCl$_3$, 300 MHz) δ 8.94 (s, 1H), 7.40 (d, J=1.8 Hz, 1H), 7.25 (s, 4H), 6.93 (dd, J=7.6, 1.8 Hz, 1H), 6.87 (d, J=7.6 HZ, 1H), 3.72 (s, 2H), 3.41 (t, 2H), 3.27 (t, 2H), 1.57 (m, 4H), 1.18–1.32 (m, 12H), 0.88 (t, t, 6H); $^{13}$C NMR (CDCl$_3$, 300 MHz) δ 171.2, 136.2, 135.0, 133.5, 129.9, 128.7, 128.6, 125.1, 122.3, 117.3, 112.5, 106.5, 48.5, 46.6, 31.8, 31.6, 29.9, 29.2, 27.9, 26.9, 26.7, 22.8, 22.7, 14.2, 14.0; mass spectrum m/z 490 (M+, 2-$^{37}$Cl) 488, 486, 415, 380, 353, 276, 274, 239, 212, 154, 128, 85.

EXAMPLE 2

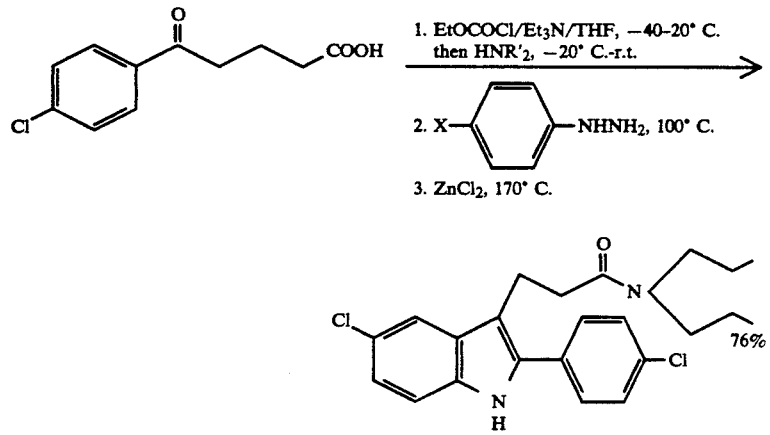

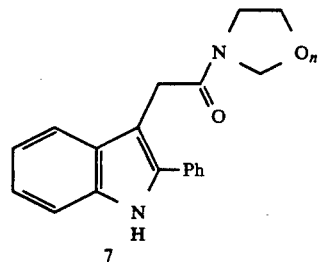

By a similar procedure as in Example 1, Compound No. 4 was prepared from 4-(4-chlorobenzoyl)butanoic acid (Compound No. 3) in 76% yield. mp 173°–174° C.; IR (KBr) 3281, 1628, 1483, 1465 cm$^{-1}$; $^1$H NMR (CDCl$_3$, 300 MHz) δ 8.10 (s, 1H), 7.59 (s, 1H), 7.46 (d, 2H), 7.43 (d, 2H), 7.27 (dd, 2H), 7.15 (dd, 2H), 3.17–3.28 (m, 4H), 3.05 (t, 2H), 2.61 (m, 2H), 1.39–1.57 (m, 4H), 0.86 (t, 3H), 0.79 (t, 3H; $^{13}$C NMR (CDCl$_3$, 300 MHz) 172.0 134.8, 134.4, 133.9, 131.1, 129.9, 129.1, 125.4, 122.7, 118.4, 112.2, 112.1, 49.7, 47.8, 33.8, 22.2, 21.0, 20.6, 11.5, 11.2; mass spectrum (15 eV) m/Z 416 (M+), 418 (M+ +2), 274, 239, 204, 142, 114, 72, 58; exact mass calcd for C$_{23}$H$_{26}$Cl$_2$N$_2$O 416.1422; found 416.1422.

EXAMPLE 3

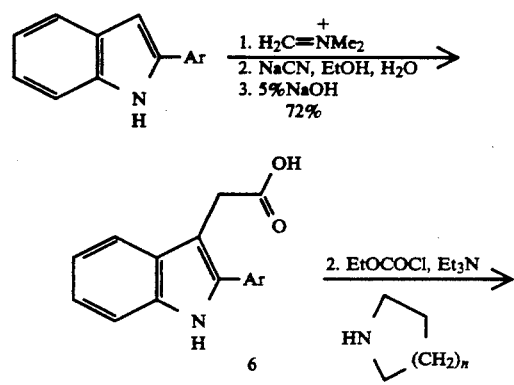

a. n = 1, 95%
b. n = 2, 51%

Synthesis of pyrrolidine and piperidine analogues 7a and 7b: 2-Phenyl-3-indoleacetic acid (6): A solution of 33 mmol of 2-phenylindole in 250 ml of chloroform was cooled to −20° C., and 102 mmol of Eschenmosers salt was added gradually. The reaction mixture was stirred for 30 minutes, and 200 ml of aqueous 5% NaOH was added. After separating, the aqueous layer was extracted with methylene chloride (2×100 ml). The combined organic layers were dried over MgSO$_4$. The solvent was removed at reduced pressure to give a solid, to which 200 ml of 95% ethanol, and 3.50 g of NaCN in 200 ml of H$_2$O were added in succession. The reaction mixture was heated to reflux for 2 hours. The cooled solution was condensed, and the residue was treated with 400 ml of 5% NaOH. The resultant suspension was heated at reflux for about 18 hour. After cooling to room temperature, the solution was made acidic by adding aqueous 12N HCl. The precipitate was collected by filtration to afford 5.83 g of Compound No. 6 (72% yield).

To a solution of 1.0 mmol of 2-phenyl-3-indoleacetic acid Compound No. 6), and 5.5 mmol of triethylamine in 30 ml of THF was added 1.0 mmol of ethyl chloroformate at −40° C. The mixture was stirred for 10 minutes at −20° C., and 1.0 mmol of pyrrolidine (or piperidine) was added. The temperature was allowed to rise to room temperature and stirring was continued for 20 minutes. Workup in the usual fashion afforded the expected products:

7a: mp 159°–160° C.; IR (KBr) 3250, 1622, 1558, 1489 cm$^{-1}$; $^1$H NMR (CDCl$_3$, 300 MHz) δ 8.12 (s, 1H), 7.69 (d, 1H), 7.59 (d, 2H), 7.48 (dd, 2H), 7.33–7.39 (m, 2H), 7.11–7.22 (m, 2H), 3.90 (s, 2H), 3.46 (m, 2H), 3.24 (m, 2H), 1.79 (m, 2H), 1.76 (m, 2H); $^{13}$C NMR (CDCl$_3$-

DMSO-d$_6$, 300 MHz) 169.9, 136.0, 135.9, 132.9, 129.1, 128.8, 128.4, 127.9, 122.4, 119.9, 119.5, 111.0, 106.3, 46.7, 46.0, 32.2, 26.2, 24.3; mass spectrum (15 ev) m/Z 304 (M+), 206, 179, 55; exact mass calcd for C$_{20}$H$_{20}$N$_2$O 304.1576; found 304.1576

7b: mp 151°-152° C.; IR (KBr) 3225, 2930, 1631, 1462 cm$^{-1}$; $^1$H NMR (CDCl$_3$, 300 MHz) δ 8.14 (s, 1H), 7.72 (d, 1H), 7.54 (d, 2H), 7.43 (dd, 2H), 7.35-7.41 (M, 2H), 7.11-7.22 (m, 2H), 3.92 (s, 2H), 3.51 (m, 2H), 3.17 (m, 2H), 1.40-1.48 (m, 4H), 1.14 (m, 2H); $^{13}$C NMR (CDCl$_3$-DMSO-d$_6$, 300 MHz) δ 168.3, 135.3, 134.6, 132.0, 127.9, 127.6, 127.4, 126.6, 120.7, 118.2, 118.1, 110.2, 104.9, 45.8, 41.9, 29.9, 25.0, 24.6, 23.4; mass spectrum (15 ev) m/Z 318 (M), 206, 203, 179, 69, 55; exact mass calcd for C$_{21}$H$_{22}$N$_2$O 318.1732; found 318.1732.

EXAMPLE 4

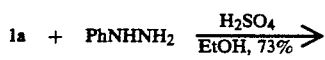

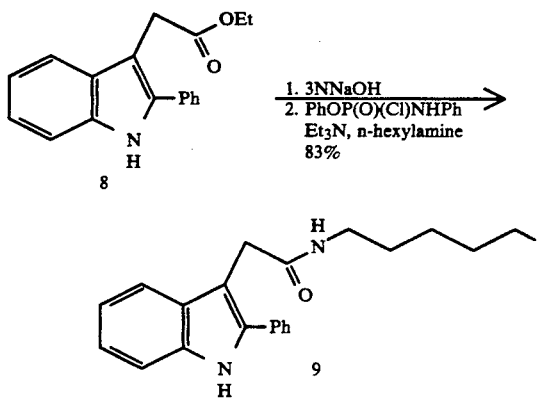

Phenylhydrazine (80 mmol), 3-benzoylpropionic acid (1a) (80 mmol), and 12 ml of concentrated H$_2$SO$_4$ in 100 ml of ethanol were heated at reflux for 24 hours. The cooled reaction mixture was poured onto 500 g of ice, and the resulting mixture was extracted with ether (300 ml×2). Workup gave a red oil, which was purified by column chromatography (silica gel, ethyl acetate/n-hexane=1/5) to afford 15.2 g (73%) of ethyl 2-phenyl-3-indole acetate (8) as a pale yellow solid. mp: 61°-62° C.; IR (KBr) 3370, 1718, 1585, 1458 cm$^{-1}$; $^1$H NMR (CDCl$_3$, 300 MHz), δ 8.17 (s, 1H), 7.67-7.71 (m, 3H), 7.47 (dd, 2H), 7.40 (dd, 2H), 7.40 (dd, 2H), 7.20 (m, 2H), 4.12 (q, 2H), 3.98 (s, 2H), 1.07 (t, 3H), mass spectrum (15 ev) m/Z 279 (M), 206, 179, 128, 102, 77, 58, 43; exact mass calcd for C$_{18}$H$_{17}$NO$_2$ 279.1259; found 279.1259.

N-Hexyl 2-phenyl-3-indoleacetamide (9). A mixture of 15 mmol of the ester Compound No. 8 in 50 ml of aqueous 3N NaOH was heated at reflux for 3 hours. The cooled reaction mixture was made acidic with 6N HCl. Ether workup gave the crude acid, which was added to a mixture of 13.5 mmol of n-hexanamine, 13.5 mmol of phenyl N-phenylphohsphoramidochloride and 27 mmol of triethylamine in 75 ml of dry methylene chloride. After stirring at ambient temperature for 1.5 hours, the solvent was removed under reduced pressure, and the residue was chromatographed (silica gel, ethyl acetate/n-hexane=⅓) to afford 4.15 g of Compound No. 9 as a white solid (83% yield from Compound No. 8); mp 113°-114° C. (recrystallization from ethyl acetate/n-hexane=1/10); IR (KBr) 3265, 3074, 1653, 1481 cm$^{-1}$; $^1$H NMR (CDCl$_3$, 300 MHz), δ 8.29 (s, 1H), 7.37-7.59 (m, 7H), 7.16-7.29 (m, 2H), 5.74 (br s, 1H), 3.84 (s, 2H), 3.18 (t, 2H), 1.61-1.97 (m, 6H), 0.82 (t, 3H); $^{13}$C NMR (CDCl$_3$, 300 MHz) 171.7, 136.7, 136.2, 132.1, 129.1, 128.8, 128.1, 127.7, 122.8, 120.3, 118.6, 111.3, 105.1, 39.6, 33.1, 31.4, 29.4, 26.4, 22.5, 13.9; mass spectrum (15 ev) m/Z 334 (M+), 206, 193, 178, 152, 128, 102, 77, 55, exact mass calcd for C$_{22}$H$_{26}$N$_2$O 334.2045; found 334.2045.

EXAMPLE 5

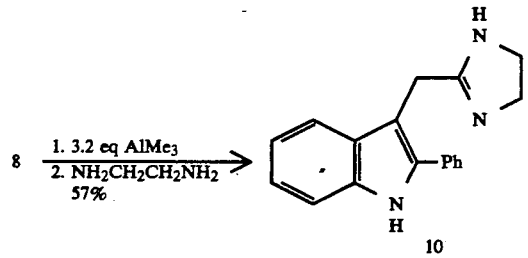

Synthesis of imidazoline derivative (10): Ethylenediamine (18 mmol) was added dropwise to a stirred solution of trimethylaluminum (2.0M in toluene, 8 mmol) in 28 ml of toluene at 10° C. The solution was allowed to warm to room temperature, and the ester Compound No. 8 (5.66 mmol) was added gradually. The reaction mixture was heated at reflux for 5.5 hours. After cooling, the solution was treated dropwise with 10 ml of H$_2$O, diluted with 30 ml of methylene chloride and 30 ml of methanol, and refluxed on a steam bath for 15 minutes. After filtration over Na$_2$SO$_4$, the solution was condensed, and the residue was allowed to pass through a short column of alumina (neutral, ethyl acetate/n-hexane=1/1 was used as eluent), to remove any remaining salt. After removal of solvent, the white solid was recrystallized from ethyl acetate/n-hexane=1/10 to afford 0.88 g (57% yield) of Compound No. 10 as fine crystals. mp 179°-180° C.; IR (KBr), 3404, 3134, 3060, 1616, 1458 cm$^{-1}$; $^1$H NMR (CDCl$_3$, 300 MHz). δ 8.40 (s, 1H), 7.58-7.63 (m, 3H), 7.46 (m, 2H), 7.39 (m, 2H), 7.21 (dd, 1H), 7.10 (dd, 1H), 3.91 (s, 2H), 3.56 (app br s, 4H); $^{13}$C NMR (CDCl$_3$, 300 MHz) 167.7, 136.4, 136.1, 132.4, 129.0, 128.9, 128.2, 127.9, 122.5, 119.9, 118.8, 112.2, 106.3, 49.9, 25.6; mass spectrum (15 ev) m/Z 275 (M+), 260, 206, 193, 178, 138, 109, 102, 77, 58, 43; exact mass calcd for C$_{18}$H$_{17}$N$_3$ 275.1422; found 275.1422.

EXAMPLE 6

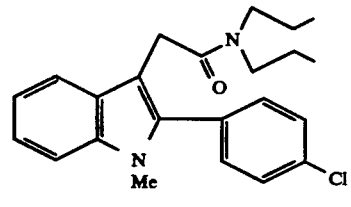

N,N-di-n-propyl 1-methyl-2-(4-chlorophenyl)-3-indole-acetamide (13). A mixture of 24.4 mmol of potassium hydroxide and 20 ml of dry dimethyl sulfoxide (DMSO) was stirred at room temperature for 15 minutes, and then 6.1 mmol of N,N-dipropyl 2-(4-chlorophenyl)-3-indolacetamide (2b) was added slowly under cooling with ice water. After stirring for 1 hour at room temperature, 12.2 mmol of methyl iodide was added. After 1.5 hours, the mixture was treated with 150 ml of H$_2$O, and the resulting mixture was extracted with ethyl acetate (50 ml×3). The combined organic layer was washed with saturated brine and dried over Na$_2$SO$_4$. Pure Compound No. 13 was obtained after removal of solvent (2.20 g, 94% yield), mp 103.5°–104.5° C. (recrystallization from n-hexane). IR (KBr) 1641, 1466, 1427 cm$^{-1}$; $^1$H NMR (CDCl$_3$, 300 MHz) δ 7.66 (d, 1H), 7.46 (d, 2H), 7.35 (d, 2H), 7.29 (d, 2H), 7.20 (m, 1H), 7.13 (dd, 1H), 3.70 (s, 2H), 3.60 (s, 3H), 3.51 (t, 2H), 3.08 (t, 2H), 1.48 (m, 4H), 0.84 (t, 3H), 0.72 (t, 3H); $^{13}$C NMR (CDCl$_3$, 300 MHz) 170.9, 137.5, 137.3, 134.4, 122.0, 130.1, 128.8, 127.8, 122.2, 119.8, 119.6, 109.4, 107.8, 49.8, 47.9, 31.1, 30.6, 23.0, 22.3, 11.4, 11.1; mass spectrum (15 ev) 382 (M+), 384 (M++2), 359, 343, 315, 269, 254, 241, 167, 71, 55; exact mass calcd for C$_{23}$H$_{27}$ClN$_2$O 382.1812; found 382.1812.

EXAMPLE 7 mass spectrum (15 ev) m/z 426 (M+), 428 (M++2), 300, 298, 218, 171, 169, 129, 102, 90; exact mass calcd for C$_{22}$H$_{27}$BrN$_2$O 426.1307; found 426.1307.

Palladium catalyze intramolecular ring closure of Compound No. 15a. A mixture of 8.8 mmol of Compound No. 15a, 0.44 mmol of tetrakis(tri-phenylphosphine)palladium, and 8.8 mmol of potassium acetate in 120 ml of dry N,N-dimethyl acetamide was heated at reflux under nitrogen gas for 36 hours. The cooled reaction mixture was allowed to pass through a short column of alumina to remove inorganic substances, and the eluent was condensed at 80° C. under reduced pressure to afford a yellow solid. The solid was chromatographed (silica gel, ethyl acetate/-hexane=⅓) to afford 2.30 g (74%) of Compound No. 16a as a White solid. mp 118°–119° C. (recrystallization from ethyl acetate/n-hexane=1/5). IR (KBr) 1635, 1468, 1425 cm$^{-1}$; $^1$H NMR (CDCl$_3$, 300 MHz) 7.96 (d, 1H), 7.71 (d, 1H), 7.38–7.47 (m, 2H), 7.26–7.34 (m, 2H), 7.14 (dd, 1H), 7.09 (dd, 1H), 5.06 (s, 2H), 4.07 (s, 2H), 3.19–3.28 (m, 4H), 0.79 (t, 3H), 0.70 (t, 3H); $^{13}$C NMR (CDCl$_3$, 300 MHz) 170.9, 141.8, 141.1, 133.6, 133.1, 132.2, 128.3, 126.9,

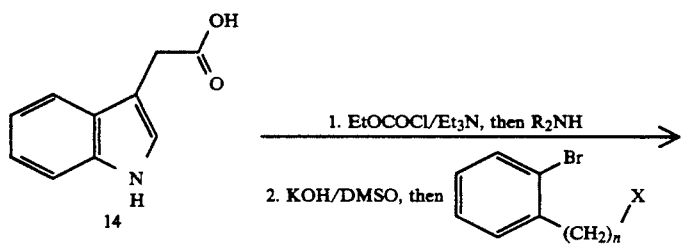

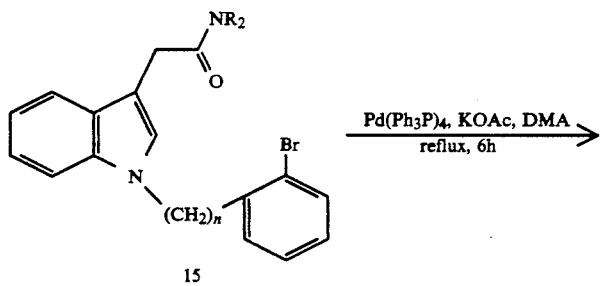

a. n = 1 (X = Br), R = n-Pr, 47%
b. n = 2 (X = I), R = n-Pr, 45%
c. n = 1 (X = Br), R = n-C$_6$H$_{13}$, 42%

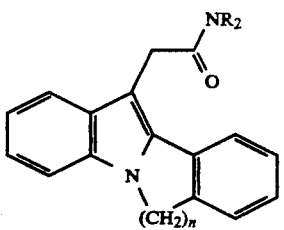

16 a. n = 1, R = n-Pr, 74%
b. n = 3, R = n-Pr, 81%
c. n = 1, R = n-C$_6$H$_{13}$, 89%

N,N-dipropyl 1-(2-bromobenzyl)-3-indoleacetamide (15a). By a procedure identical to that of Example 2, N,N-dipropyl indoleacetamide was obtained from indoleacetic acid (14) in 48% yield, which was combined with 0-bromobenzyl bromide to afford Compound No. 15a in 94% yield. IR (Nujol) 1641, 1588, 1489 cm$^{-1}$; $^1$H NMR (CDCl$_3$, 300 MHz) δ 7.64 (d, 1H), 7.58 (dd, 1H), 7.06–7.25 (m, 6H), 6.58 (br, 1H), 5.34 (s, 2H), 3.82 (s, 2H), 3.33 (t, 2H), 3.22 (t, 2H), 1.55 (m, 4H), 0.85 (t, 6H);

123.5, 122.0, 121.7, 119.9, 119.5, 109.2, 100.3, 49.9, 48.3, 47.9, 31.8, 22.2, 20.9, 11.4, 11.1; mass spectrum (15 ev) m/z 346 (M+), 218, 159, 128, 109, 99, 84, 69, 55; exact mass calcd for C$_{23}$H$_{26}$N$_2$O 346.2045; found 346.2045.

PHARMACOLOGICAL STUDIES

A) Binding Studies

Mitochondrial Preparation: Sprague Dawley rats (200–250 gr.) were killed by decapitation. Brain and adrenal glands were removed and homogenized with Polytron for 15 minutes in ice cold buffer (10 mM Na/KPO$_4$, 0.32M sucrose, pH 7.4). The homogenate was centrifuged for 15 minutes at 6,500 xg at 4° C. The resulting supernatant was centrifuged for 15 minutes at 6500 xg at 4° C. The pellet was suspended in buffer (20 times) by gentle homogenization and centrifuged at 10,000 xg at 4° C. for 15 minutes. The washed mitochondrial pellet was stored at −70° C.

For the binding assay the mitochondrial fraction was diluted with 50 mM Na/KPO$_4$ buffer (pH 7.4) to give a final protein concentration of 100g in 100 μl buffer. This suspension was incubated with 1 nM of $^3$H PK-11195 or $^3$H RO 5-4864 (50 μl) with or without 10/μM unlabeled PK-11195 or RO 5-4864 to assess the extent of total and non-specific binding. Different amounts of indole derivatives were added to the incubation medium in a volume of 50 μl. After incubation for 60 minutes at 4° C., samples were filtered and the radioactivity was measured in a scintillation counter.

Crude Synaptic Membrane Preparation: Sprague Dawley rats (200–250 gr.) were killed by decapitation. The cerebella were removed and incubated for 20 minutes in ice cold double distilled water after homogenization with Polytron. The homogenate was centrifuged at 18,000 xg at 4° C. for 10 minutes. The pellet was suspended in ice-cold buffer 50 mM Na/KPO$_4$ (pH 7.4) and centrifuged at 18,000 xg at 4° C. for 10 minutes. After two other centrifugations, the membranes were suspended in 5 ml of buffer and the proteins were measured.

The membranes were diluted with 50 mM Na/KPO$_4$ buffer (pH 7.4) to a concentration of 150 μg of protein/ml, and 150 μl aliquots of the suspension were incubated with 50 μl of the different ligands to be tested: $^3$H-ZOLPIDEM(2 nM), $^3$H-FLUMAZENIL (2 nM), $^3$H-GABA(10 nM), $^3$H-MK 801(5 nM), $^3$H-KETANSERIN(1 nM), $^3$H-GLYCINE(20 nM), $^3$H-SPIPERONE(1 nM), $^3$H-AMPA(10 nM), $^3$H-3-PPP(1 nM), and $^3$H-NALOXONE(1 nM). Non-specific binding was assessed by displacing with 10 to 1000/μM of cold ligand. The different indole derivatives were added in a volume of 50 μl in a concentration varying from $10^{-9}$ to $10^{-3}$M. The results are reported in Table I hereinbelow.

TABLE I
BINDING CHARACTERISTICS OF INDOLE DERIVATIVES
| STRUCTURE | #* | ³H-PK11195 IC50 (nM) | ³H-RO5-4864 IC50 (nM) | ³H-PK11195 / ³H-RO5-4864 | ³H-ZOLPIDEM IC50 (nM) | ³H-FLUMAZENIL IC50 (nM) | ³H-GABA IC50 (nM) |
|---|---|---|---|---|---|---|---|
| 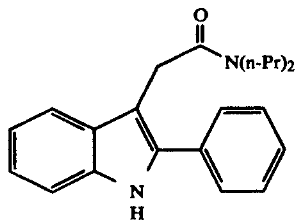 | 2 | 32.5 (45–20) | 22.5 (30–15) | 1.4 | >1000 | >1000 | >1000 |
| 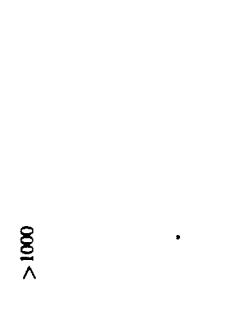 | 3 | 84 | 59 | 1.4 | >1000 | | |
| 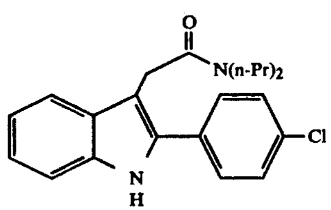 | 5 | 28.5 (7–50) | 25.5 (11–40) | 1.1 | >1000 | >1000 | |
| 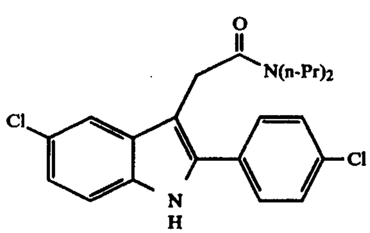 | 6 | 45 | 40 | 1.1 | >1000 | >1000 | |

TABLE I-continued

BINDING CHARACTERISTICS OF INDOLE DERIVATIVES

| # | STRUCTURE | ³H-PK11195 IC50 (nM) | ³H-RO5-4864 IC50 (nM) | ³H-PK11195 / ³H-RO5-4864 | ³H-ZOLPIDEM IC50 (nM) | ³H-FLUMAZENIL IC50 (nM) | ³H-GABA IC50 (nM) |
|---|---|---|---|---|---|---|---|
| 7 | 2-phenyl-indole-3-CH₂C(O)NMe₂ | 600 | 600 | 1 | >1000 | >1000 | |
| 8 | 5-Me-2-(4-Me-phenyl)-indole-3-CH₂C(O)N(n-Pr)₂ | 68.5 (60–77) | 41.5 (50–33) | 1.6 | >1000 | | |
| 9 | 5-Me-2-(4-Me-phenyl)-indole-3-CH₂C(O)NMe₂ | >1000 | 255 (300–210) | >3 | >1000 | | |
| 10 | 2-(2-thienyl)-indole-3-CH₂C(O)N(n-Pr)₂ | 24 (30–18) | 14.5 (20–8) | 1.6 | >1000 | | |

TABLE I-continued
BINDING CHARACTERISTICS OF INDOLE DERIVATIVES

| STRUCTURE | #* | ³H-PK11195 IC50 (nM) | ³H-RO5-4864 IC50 (nM) | ³H-PK11195 ³H-RO5-4864 | ³H-ZOLPIDEM IC50 (nM) | ³H-FLUMAZENIL IC50 (nM) | ³H-GABA IC50 (nM) |
|---|---|---|---|---|---|---|---|
| (2-(4-chlorophenyl)-5-chloroindol-3-yl with N(n-Pr)₂ amide) | 11 | 180 | 120 | 1.5 | >1000 | >1000 | |
| (2-phenylindol-3-yl acetamide with n-heptyl NH) | 13 | 57.5 (50-65) | 32.5 (20-45) | 1.8 | | >1000 | >1000 |
| (2-phenylindol-3-yl methyl imidazoline) | 15 | >1000 | >1000 | | | >1000 | |
| (N-methylcarbazol-1-yl acetamide with N(n-Pr)₂) | 16 | 30 | 40 | 0.75 | | >1000 | >1000 |

TABLE I-continued
BINDING CHARACTERISTICS OF INDOLE DERIVATIVES
| # | STRUCTURE | ³H-PK11195 IC50 (nM) | ³H-RO5-4864 IC50 (nM) | ³H-PK11195 ³H-RO5-4864 | ³H-ZOLPIDEM IC50 (nM) | ³H-FLUMAZENIL IC50 (nM) | ³H-GABA IC50 (nM) |
|---|---|---|---|---|---|---|---|
| 17 | 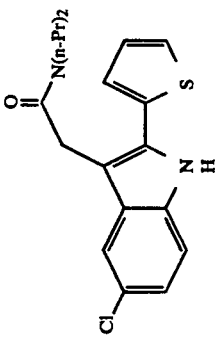 | 50 (30–70) | 37.5 (40–35) | 1.3 | | >1000 | |
| 18 | 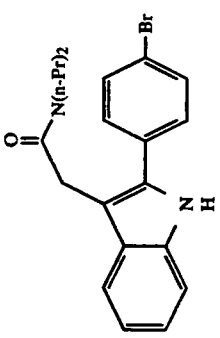 | 75 | 36 | 2 | | >1000 | |
| 19 | 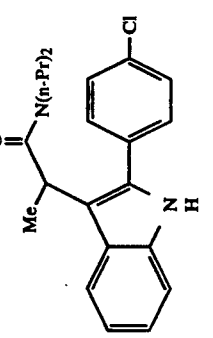 | >1000 | >1000 | | | >1000 | |
| 20 | 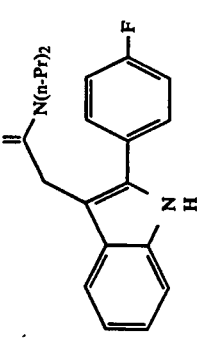 | 100 | 50 | 2 | | >1000 | >1000 |

TABLE I-continued
BINDING CHARACTERISTICS OF INDOLE DERIVATIVES
| STRUCTURE | #* | ³H-PK11195 IC50 (nM) | ³H-RO5-4864 IC50 (nM) | ³H-PK11195 ³H-RO5-4864 | ³H-ZOLPIDEM IC50 (nM) | ³H-FLUMAZENIL IC50 (nM) | ³H-GABA IC50 (nM) |
|---|---|---|---|---|---|---|---|
| 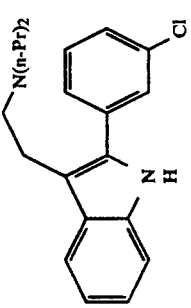 | 21 | 100 | 80 | 1.2 | | >1000 | >1000 |
| 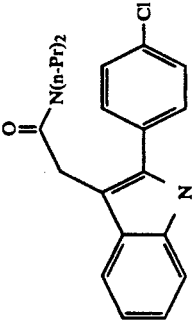 | 22 | 200 | 200 | 1 | | >1000 | |
| 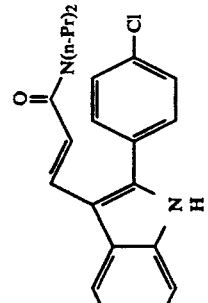 | 24 | 700 | 600 | 1.1 | >1000 | >1000 | |
| 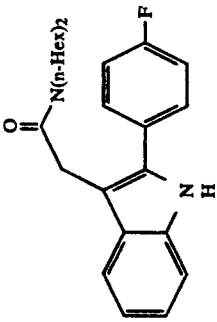 | 27 | 18 | 20 | 0.9 | — | >1000 | >1000 |

TABLE I-continued
BINDING CHARACTERISTICS OF INDOLE DERIVATIVES
| STRUCTURE | #* | 3H-PK11195 IC50 (nM) | 3H-RO5-4864 IC50 (nM) | 3H-PK11195 3H-RO5-4864 | 3H-ZOLPIDEM IC50 (nM) | 3H-FLUMAZENIL IC50 (nM) | 3H-GABA IC50 (nM) |
|---|---|---|---|---|---|---|---|
| 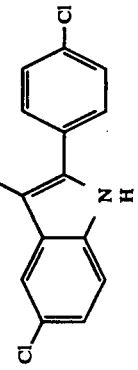 | 43 | 12 | 15 | 0.8 | — | >1000 | >1000 |
*Numbers assigned to compounds in pharmacological studies are not the same numbers set forth in the preparation examples.

RESULTS

Table I indicates that most of the indole derivatives tested potently displace $^3$H-PK 11195 or $^3$H-RO5-4864 from MBR. Similar results were obtained in mitochondria obtained from brain or adrenal glands. No displacements were observed when studying the binding of $^3$H-FLUMAZENIL- a specific ligand for the BZD binding site located on the GABA$_A$ receptor, $^3$H-SPIROPERIDOL- a ligand for dopamine and 5HT receptors, $^3$H-KETANSERIN- a specific ligand for the 5HT$_2$ receptor, $^3$H-MK 801- a ligand for the NMDA selective glutamate receptor, $^3$H-AMPA- a ligand selective for the low conductance glutamate receptor, $^3$H-3 PPP- a ligand for the sigma receptor, $^3$H-SERINE- a ligand for the strychnine insensitive recognition site located on the NMDA selective glutamate receptor, or $^3$H-NALOXONE- a ligand for opioid binding sites.

B) Pregnenolone Formation in Glial Mitochondria

Mitochondria from C6-2B glioma cells were prepared as described in Krueger and Papadopoulos, *J. Biol. Chem.* 265:15015–15022 (1990). For the measurement of mitochondrial steroid biosynthesis, the effect of different MBR ligands on the mitochondria of C6-2B glioma cells was determined as previously described in Papadopoulos et al., *J. Biol. Chem.* 265:3772–3779 (1990). In brief, mitochondria were resuspended at a concentration of 0.4–0.8 mg of protein per 400 μl of buffer A (20 mM Tris-HCl (pH 7.4), 0.25M sucrose, 5 mM MgCl$_2$, 20 mM KCl) containing 5/μM trilostane, an inhibitor of pregnenolone metabolism (Papadopoulos et al., 1990). The mixture was preincubated for 5 minutes at 37° C. The incubation mixture was extracted with 5 ml chloroform/methanol (2:1, vol/vol), and the organic phase was evaporated to dryness. Pregnenolone was measured by a specific radioimmunoassay using an antibody obtained from Radioassay Systems Laboratories, Carson, Calif. The results are reported in Table II hereinbelow.

TABLE II

EFFECTS OF INDOLE-DERIVATIVES ON MITOCHONDRIAL PREGNENOLONE FORMATION FROM GLIAL CELLS

| Drug # | EFFECTIVE CONCENTRATION | | STIMULATION |
|---|---|---|---|
| | Maximal | 50% | % |
| 2 | $10^{-9}$M | $3.3 \times 10^{-10}$M | 200 |
| 7 | $10^{-7}$M | $10^{-8}$M | 131 |
| 8 | $10^{-7}$M | $3.3 \times 10^{-8}$M | 220 |
| 9 | $>10^{-6}$ | — | none |
| 20 | $10^{-9}$M | $3.3 \times 10^{-10}$M | 183 |
| 22 | $10^{-8}$M | — | 170 |
| 27 | $10^{-7}$M | $3.3 \times 10^{-9}$M | 300 |

C6 glial cell mitochondria were incubated with increasing concentrations of the indicated drugs for 15 minutes at 37° C. under the conditions described under the Methods section herein. At the end of the incubation period, pregnenolone formed was extracted and measured by radioimmunoassay.

Table II shows the maximal effective concentrations of some of the compounds used in stimulating glial cell mitochondrial pregnenolone formation. The percentage of increase, over the control, of steroid synthesis is also given. It can been clearly observed that indole compounds with high affinity for MBR are the most efficacious and potent in increasing pregnenolone formation (compare these data with those of Table I). Moreover some compounds (e.g., Compound No. 7) which bind to MBR with relatively high affinity but which have low intrinsic efficacy, could be considered as candidates as partial agonist drugs.

C) Elevated X Maze Test

The elevated X maze is a behavioral test to detect anxiolytic drugs in rodents. The test is described in Hughes et al., PNAS 87:6728–6732 (1990). The plus-maze consists of two open arms (43×8 cm) and two similarly sized enclosed arms with 9 cm high walls, arranged so that the arms of the same type are opposite each other. There is a central square of 8 cm. The apparatus is elevated to a height of 10 cm and each arm is divided into 3 squares.

Sprague Dawley rats weighing 200–250 gr. were housed in a room with a 12 hour light: 12 hour dark cycle and were allowed free access to food and water. After an i.v. injection of different indole derivatives, the rats were kept separated for 10, 20 or 30 minutes before testing. The testing period commenced when each animal was placed onto the central square of the maze. The number of entries in each arm was then recorded for 5 minutes. The maze was cleaned with water after each trial. The number of entries in the open arms provided a measure of anxiolytic activity of the drugs. The results are reported in Table III hereinbelow.

TABLE 3

ELEVATED X MAZE TEST IN RATS

| # | DOSE mg/kg | TEST AFTER 10 MIN INJECTION ENTRIES IN OPEN ARMS | TEST AFTER 20 MIN INJECTION ENTRIES IN OPEN ARMS | TEST AFTER 30 MIN INJECTION ENTRIES IN OPEN ARMS |
|---|---|---|---|---|
| 2 | 200 | 4 | 0 | 0 |
| 2 | 20 | 0 | 0 | 0 |
| 13 | 20 | 2 | 2 | 3 |
| 18 | 20 | 2 | not performed | not performed |
| 19 | 20 | 1 | " | " |
| 20 | 20 | 3 | 2 | 6 |
| 21 | 20 | 2 | 4 | 0 |
| 22 | 20 | 3 | 2 | 6 |
| 24 | 20 | 3 | 2 | 3 |
| 27 | 0.5 | 5 | 2 | 1 |
| 43 | 0.5 | 4 | 2 | 1 |

Table III indicates that some indole derivatives (Compound Nos. 2, 13, 18, 19, 20, 21, 22, 24, 27 and 43) increase the behavioral output in rats subjected to the elevated X maze test. For some of these drugs the effect is protracted for more than 30 minutes. Since this test has been used to reveal anxiolytic properties of drugs (see the Methods section herein) it can be inferred that indole derivatives may be anxiolytic drugs. The most potent anxiolytic drugs are the compounds 27 and 43. These drugs possess anxiolytic action in the elevated X-maze for doses as small as 0.1 to 0.5 mg/kg. These doses are 100 to 500-fold lower than the doses that produce sedation, and ataxia in rats. For compounds that cross the blood-barrier, the anxiolytic effect correlates with their binding affinity to the MBRs and their potency and efficacy to stimulate steroidogenesis.

Pharmacological Effects

The results show that by activating MBR with the compounds of the present invention, one can increase neurosteroid production by glial mitochondria. As a result, the compounds of the present invention are useful in treating neurological and psychiatric disorders (neuro-psychiatric disorders), such as epilepsy, dyskinesia, Parkinson's disease, Huntington's chorea of different types, encephalopathies, schizophrenia, depression, anxiety, panic, and obsessive-compulsive disorders.

Pharmaceutical Compositions

The compounds of the present invention may be formulated into pharmaceutical compositions by combination with appropriate, pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration.

The compounds can be used alone, in combination with each other, or they can be used in combination with other anti-psychotic or neurological agents.

The following methods and excipients are merely exemplary and are in no way limiting.

In pharmaceutical dosage forms, the compounds of the present invention may be used in the form of their pharmaceutically acceptable salts, or they may also be used alone or in appropriate association, as well as in combination with other pharmaceutically active compounds.

In the case of oral preparations, the compounds of the present invention may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the present invention may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds of the present invention can be utilized in aerosol formulation to be administered via inhalation. The compounds of the present invention can be formulated into pressurized acceptable propellants such as dichlorodifluoromethane, propane, nitrogen and the like.

Furthermore, the compounds of the present invention may be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, e.g., teaspoonful, tablespoonful, tablet or suppository contains a predetermined amount of the composition containing one or more compounds of the present invention; similarly, unit dosage forms for injection or intravenous administration may comprise the compound of the present invention in a composition as a solution in sterile water, normal saline or another pharmaceutically acceptable carrier The term "unit dosage form" as used herein refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, for example vehicles, adjuvants, carriers or diluents, are readily available to the public.

One skilled in the art can easily determine the appropriate method of administration for the exact formulation of the composition being used. Any necessary adjustments in dose can be made readily to meet the nature or severity of the condition and adjusted accordingly by the skilled practitioner.

The present invention relates further to a method of treating neurological and psychiatric disorders which comprises administering an effective amount of the compound in order to achieve the desired effect, e.g., in treating psychoses or anxiety, an anti-psychotic or anti-anxiety effective amount, respectively. The actual dose and schedule for drug administration for each patient will vary depending upon individual differences in pharmacokinetics, drug disposition and metabolism. Moreover, the dose may vary when the compounds are used in combination with other drugs. Such dosage amounts can be readily ascertained without undue burden and experimentation by those skilled in the art.

As an example of a therapeutically effective amount for treating anxiety, depression and/or schizophrenia, the dosage for humans can range from about between 0.01 mg/kg body weight to 200 mg/kg body weight.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A compound having the formula:

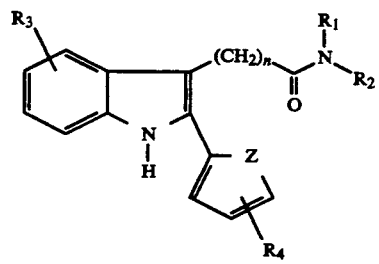

wherein $R_1$ and $R_2$ independently is selected from the group consisting of H, $C_3$–$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is H, $C_1$–$C_{12}$ straight or branched alkyl, $NO_2$, $NH_2$, $N_3$, CN, halogen, $CO_2R$, OR, or SR wherein R is H or lower alkyl;

$R_4$ is H, $C_1$–$C_{12}$ straight or branched alkyl, $NO_2$, $NH_2$, $N_3$, CN, halogen, $CO_2R$, OR, or SR wherein R is H or lower alkyl;

Z is O, NH, S or —CH=CH—; and n is an integer of 1–3; or a pharmaceutically acceptable salt thereof.

2. The compound according to claim 1 having the formula

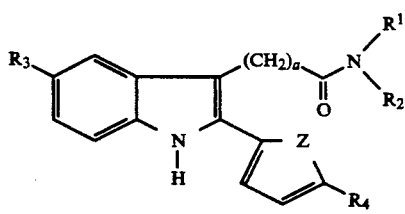

wherein $R_1$ and $R_2$ independently is selected from the group consisting of H, $C_1$–$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is H, $C_1$–$C_{12}$ straight or branched alkyl, $NO_2$, $NH_2$, $N_3$, CN, halogen, $CO_2R$, OR, or SR wherein R is H or lower alkyl;

$R_4$ is H, $C_1$–$C_{12}$ straight or branched alkyl, $NO_2$, $NH_2$, $N_3$, CN, halogen, $CO_2R$, OR, or SR wherein R is H or lower alkyl;

Z is O, $NH_2$, S, or —CH=CH—; and n is an integer of 1–3; or a pharmaceutically acceptable salt thereof.

3. The compound according to claim 1 having the formula

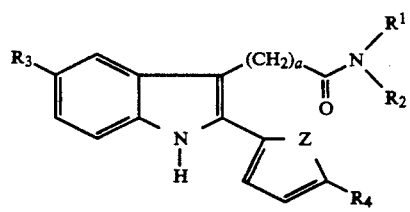

wherein $R_1$ and $R_2$ independently is selected from the group consisting of H, $C_3$–$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is $C_1$–$C_{12}$ straight or branched alkyl, $NO_2$, $NH_2$, $N_3$, CN, halogen, $CO_2R$, OR, or SR wherein R is H or lower alkyl;

Z is O, NH, S, or —CH=CH—; and n is an integer of 1–3; or a pharmaceutically acceptable salt thereof.

4. The compound according to claim 1 having the formula

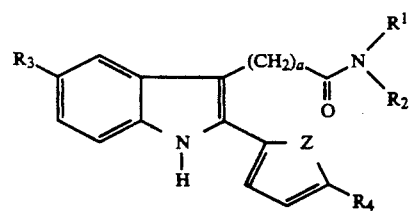

wherein $R_1$ and $R_2$ independently is selected from the group consisting of H, $C_4$–$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is H, $C_1$–$C_{12}$ straight or branched alkyl, $NO_2$, $NH_2$, $N_3$, CN, halogen, $CO_2R$, OR, or SR wherein R is H or lower alkyl;

$R_4$ is H, $C_1$–$C_{12}$ straight or branched alkyl, $NO_2$, $NH_2$, $N_3$, CN, halogen, $CO_2R$, OR, or SR wherein R is H or lower alkyl;

Z is O, NH, S, or —CH=CH—; and n is an integer of 1–3; or a pharmaceutically acceptable salt thereof.

5. The compound according to claim 1, wherein $R_3$ is $C_1$–$C_{12}$ straight or branched alkyl and $R_4$ is halogen.

6. The compound according to claim 2, wherein $R_3$ is $C_1$–$C_{12}$ straight or branched or alkyl or halogen and $R_4$ is $C_1$–$C_{12}$ straight or branched alkyl or halogen.

7. The compound according to claim 1, wherein $R_1$ and $R_2$ are both independently $C_4$–$C_{10}$ straight or branched alkyl.

8. The compound according to claim 2, wherein $R_1$ and $R_2$ are both independently $C_4$–$C_{10}$ straight or branched alkyl.

9. The compound according to claim 3, wherein $R_3$ is $C_1$–$C_{12}$ straight or branched alkyl or halogen and $R_4$ is $C_1$–$C_{12}$ straight or branched alkyl or halogen.

10. The compound according to claim 3, wherein $R_1$ and $R_2$ both are $C_3$–$C_{12}$ straight or branched chain alkyl.

11. The compound according to claim 2, wherein $R_3$ is $C_1$–$C_{12}$ straight or branched alkyl or halogen, $R_4$ is $C_1$–$C_{12}$ straight or branched alkyl or halogen, and $R_1$ and $R_2$ are $C_3$–$C_{12}$ straight or branched alkyl.

12. The compound according to claim 2 having the formula

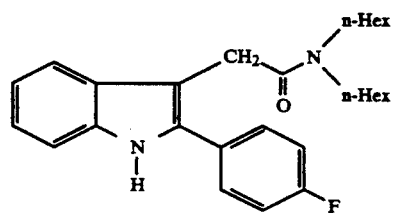

13. The compound according to claim 2 having the formula

14. The compound according to claim 2 having the formula

[structure: indole with 2-thienyl at 2-position, 3-CH2-C(O)-N(n-Pr)2]

[structure: 5-chloro-indole with 2-(4-chlorophenyl) at 2-position, 3-CH2-C(O)-N(n-Hex)2]

15. A pharmaceutical composition which comprises an antianxiety effective amount of a compound having the formula:

[structure with R3, R1, R2, R4, Z, (CH2)n]

wherein $R_1$ and $R_2$ independently is selected from the group consisting of $C_3$–$C_{12}$ straight or branched alkyl, aryl or lower alkyl-substituted aryl; or $R^1$ and $R^2$ may be joined to form a 4-to 6-membered saturated or unsaturated ring or a 4-to 6-membered saturated or unsaturated lower alkyl-substituted ring;

$R_3$ is H, $C_1$–$C_{12}$ straight or branched alkyl, $NO_2$, $NH_2$, $N_3$, CN, halogen, $CO_2R$, OR, or SR wherein R is H or lower alkyl;

$R_4$ is H, $C_1$–$C_{12}$ straight or branched alkyl, $NO_2$, $NH_2$, $N_3$, CN, halogen, $CO_2R$, OR, or SR wherein R is H or lower alkyl;

Z is O, NH, S or —CH=CH—;

and n is an integer of 1–3; or a pharmaceutically acceptable salt thereof; and a pharmaceutically acceptable carrier.

16. The composition according to claim 15, wherein said anti-anxiety effective amount is from about 0.01 to 200 mg/kg body weight.

17. A method of treating psychiatric or neurological disorders which comprises administering to a patient in need thereof, a therapeutically effective amount of a compound having the formula:

[structure with R3, R1, R2, R4, Z, (CH2)n]

wherein $R_1$ and $R_2$ independently is selected from the group consisting of H, $C_1$–$C_{12}$ straight or branched alkyl, aryl or lower alkyl-substituted aryl; or $R_1$ and $R_2$ may be joined to form a 4-to 6-membered saturated or unsaturated ring or a 4-to 6-membered saturated or unsaturated lower alkyl-substituted ring;

$R_3$ is H, $C_1$–$C_{12}$ straight or branched alkyl, $NO_2$, $NH_2$, $N_3$, CN, halogen, $CO_2R$, OR, or SR wherein R is H or lower alkyl;

$R_4$ is H, $C_1$–$C_{12}$ straight or branched alkyl, $NO_2$, $NH_2$, $N_3$, CN, halogen, $CO_2R$, OR, or SR wherein R is H or lower alkyl;

Z is O, NH, S or —CH=CH—; and n is an integer of 1–3; or a pharmaceutically acceptable salt thereof.

18. The method according to claim 17, wherein $R_1$ and $R_2$ independently is $C_3$–$C_{12}$ straight or branched alkyl.

19. The method according to claim 17, wherein said therapeutically effective amount is from about 0.01 to 200 mg/kg body weight.

20. The method according to claim 17, wherein said psychiatric disorder is schizophrenia.

21. The method according to claim 17, wherein said psychiatric disorder is depression.

22. The method according to claim 17, wherein said psychiatric disorder is anxiety.

23. The method according to claim 17, wherein said neurological disorder is Parkinson's disease.

* * * * *